United States Patent
Chi et al.

(10) Patent No.: US 10,640,447 B1
(45) Date of Patent: May 5, 2020

(54) PROCESS FOR HYDROGENATION OF AROMATIC POLYCARBOXYLIC ACIDS OR DERIVATIVES THEREOF TO THE CORRESPONDING ALICYCLIC POLYCARBOXYLIC ACIDS OR DERIVATIVES THEREOF

(71) Applicant: CPC Corporation, Taiwan, Kaohsiung (TW)

(72) Inventors: Ching-Fa Chi, Chiayi (TW); Ying-Chien Yang, Chiayi (TW); Yi-Hui Chen, Chiayi (TW); Jeng-Fan Leu, Chiayi (TW); Shiann-Horng Chen, Chiayi (TW); Yih-Ping Wang, Chiayi (TW); Chyi-Liuh Ho, Chiayi (TW)

(73) Assignee: CPC CORPORATION, TAIWAN, Kaohsiung (TW)

( * ) Notice: Subject to any disclaimer, the term of this patent is extended or adjusted under 35 U.S.C. 154(b) by 0 days.

(21) Appl. No.: 16/353,839

(22) Filed: Mar. 14, 2019

(30) Foreign Application Priority Data

Feb. 13, 2019 (TW) .............................. 108104750 A

(51) Int. Cl.
| | | |
|---|---|---|
| *C07C 67/303* | (2006.01) | |
| *B01J 21/16* | (2006.01) | |
| *B01J 27/25* | (2006.01) | |

(52) U.S. Cl.
CPC ............. *C07C 67/303* (2013.01); *B01J 21/16* (2013.01); *B01J 27/25* (2013.01)

(58) Field of Classification Search
CPC .......... C07C 67/303; B01J 27/25; B01J 21/16
See application file for complete search history.

(56) References Cited

U.S. PATENT DOCUMENTS

| | | | |
|---|---|---|---|
| 6,049,008 A * | 4/2000 | Roberts .................... | B01J 21/16 564/420 |
| 6,284,917 B1 | 9/2001 | Brunner et al. | |
| 7,595,420 B2 | 9/2009 | Schlosberg et al. | |
| 8,586,784 B2 | 11/2013 | Grass et al. | |
| 8,722,922 B2 | 5/2014 | Chang et al. | |

FOREIGN PATENT DOCUMENTS

CN 102658182 B 4/2014

* cited by examiner

*Primary Examiner* — Jafar F Parsa
*Assistant Examiner* — Blaine G Doletski
(74) *Attorney, Agent, or Firm* — Chun-Ming Shih

(57) ABSTRACT

This invention discloses the process for hydrogenation of aromatic polycarboxylic acids or derivatives thereof, hydrogenation of aromatic polycarboxylic acids or derivatives thereof can be achieved in the present of the catalyst, which consist at least one metal of the eighth transition group of the Periodic Table as the active metal while group IIA and group IVA elements are included as the catalyst support.

25 Claims, No Drawings

PROCESS FOR HYDROGENATION OF AROMATIC POLYCARBOXYLIC ACIDS OR DERIVATIVES THEREOF TO THE CORRESPONDING ALICYCLIC POLYCARBOXYLIC ACIDS OR DERIVATIVES THEREOF

FIELD OF THE INVENTION

The present disclosure relates to a process for hydrogenation of aromatic polycarboxylic acids or derivatives thereof to the corresponding alicyclic polycarboxylic acids or derivatives thereof.

BACKGROUND OF THE INVENTION

Hydrogenation, a reaction of reducing carbon-carbon double bonds to saturated alkanes in hydrogen atmosphere with the presence of a catalyst, is common in processes of oil refining, food, pharmaceutical manufacturing, and chemical commodity. For example, removing sulfur, nitrogen, nickel or vanadium from oil by hydrogenation; reducing the unsaturated fat in vegetable oil through hydrogenation; adding hydrogen to unsaturated chain segments of copolymers to transform the molecular structures and characteristics such as hydrogenation of benzene rings can reduce UV degradation of aromatic epoxy resins. Hydrogenated alicyclic polycarboxylic acids have been used in functional polyimide or functional epoxy resin hardeners; hydrogenated cyclohexane dicarboxylic acid ester can replace phthalate to serve as a plasticizer in PVC processing or as a coating material, a filling and reinforcing material or a processing agent. For PVC processing, currently, PAE (phthalate ester) series products/derivatives such as dibutyl phthalate (DBP), dioctyl phthalate (DOP) or diisononyl phthalate (DINP) have been widely used as plasticizers. However, such substances, denounced as hazardous substances in recent years, have been prohibited to be used in some child and/or infant products gradually. Therefore, phthalate has been replaced by some alicyclic dicarboxylic acid esters that are regarded as environment-friendly substances in applications of plasticizers. For example, 1, 2-Cyclohexane dicarboxylic acid diisononyl ester (DINCH) is normally produced, as described in the prior art, by saturating the benzene rings of polycarboxylic acids or their derivatives through hydrogenation, which also remove the toxicity of them.

The catalyst used for hydrogenation reaction is a considerable issue. In the prior art, the U.S. Pat. No. 6,284,917B1 discloses that bimodal alumina with macropores is selected as a support for production of supported ruthenium catalyst to produce corresponding alicyclic carboxylic esters using a high pressure batchwise stirred reactor (autoclave) at 80° C. and 100-200 bar.

The Chinese Patent, CN102658182B, discloses that phosphorus-modified alumina (P—$Al_2O_3$) can be used as a support and loaded with nickel to give a catalyst which can be used in production of corresponding alicyclic carboxylic esters in a continuous fixed-bed reactor at temperature from 150 to 200° C. and pressure between 30 and 150 bar.

The U.S. Pat. No. 7,595,420B2, discloses a silica material with ordered pores, MCM-41, can be used as a catalyst support for production of supported ruthenium catalysts and used to give corresponding alicyclic carboxylic esters at 120° C. and 58 to 200 bars using a high pressure batchwise stirred reactor (autoclave).

The U.S. Pat. No. 8,722,922B2, discloses a supported catalyst, group VIIIB transition metals such as Pd and Ru loaded on 2A-alumina support (2A-$Al_2O_3$), can be used in production of corresponding alicyclic carboxylic esters in a fixed-bed reactor at temperature from 100 to 250° C. and pressure between 1 and 50 bar.

The U.S. Pat. No. 8,586,784B2, discloses a supported catalyst prepared with titanium dioxide ($TiO_2$, as a support) can be used in production of corresponding alicyclic carboxylic esters in a continuous fixed-bed reactor at 100° C. and pressure of 100 bar.

According to the above-mentioned prior art, in most of the inventions, to make the hydrogenation rate of benzene rings reach higher than 90%, the hydrogenation of aromatic polycarboxylic acid esters needs be carried out under the condition of high pressure (>100 bar) or high temperature (higher than 100° C.) or both high pressure and high temperature which leads to the high cost of investment and the high cost of subsequent operation and maintenance.

SUMMARY OF THE INVENTION

The present disclosure provides a process for hydrogenation of aromatic polycarboxylic acids or derivatives thereof to give the corresponding alicyclic polycarboxylic acids or derivatives thereof. The process can be carried out at low pressure (<30 Bars) and low temperature (<80° C.), and the conversion and selectivity reach greater than 99.9% and 99.4%, respectively.

Aromatic polycarboxylic acids in the present disclosure broadly refer to aromatic compounds form with carboxylic acids, dicarboxylic acids, polycarboxylic acids or hydroxycarboxylic acids in structure. Aromatic chain segments comprise benzenes, biphenyls, anthracenes, naphthalenes, polycyclic aromatic hydrocarbons, etc., such as benzene polycarboxylic acids, biphenyl polycarboxylic acids, naphthalene polycarboxylic acids, etc., and thus hydrogenation reaction of the benzene rings portion of different aromatic polycarboxylic acids or derivatives thereof can be carried out to produce saturated corresponding alicyclic polycarboxylic acids or derivatives thereof, particularly refer to hydrogenation reaction of the benzene rings portion of the benzene polycarboxylic acids or derivatives thereof to produce cyclohexane polycarboxylic acids or derivatives thereof. Benzene polycarboxylic acids comprise phthalic acids, isophthalic acids, terephthalic acids, trimellitic acids, trimesic acids, hemimellitic acids, pyromellitic acids, or any combination of the above.

Derivatives of aromatic polycarboxylic acids comprise monoesters, diesters or polyesters of aromatic polycarboxylic acids wherein the esters comprise $C_1$-$C_{30}$ alkyl esters, $C_3$-$C_{30}$ cycloalkyl esters and $C_1$-$C_{30}$ alkoxyalkyl esters, and preferably are $C_2$-$C_{20}$ alkyl esters, $C_3$-$C_{20}$ cycloalkyl esters and $C_2$-$C_{20}$ alkoxyalkyl esters, and further preferably are $C_3$-$C_{18}$ alkyl esters, $C_4$-$C_{18}$ cycloalkyl esters, $C_3$-$C_{18}$ alkoxyalkyl esters, and wherein a carbon chain is a linear chain or a branched chain. For example, dimethyl phthalate (DMP), dimethyl terephthalate (DMT), dimethyl isophthalate (DMI), diethyl phthalate (DEP), dibutyl phthalate (DBP), diisooctyl phthalate (DOP), diisononyl phthalate (DINP), benzyl butyl phthalate (BBP), diisodecyl phthalate (DIDP), dioctyl terephthalate (DOTP) or any combination of the above.

The present invention provides a process for hydrogenation of aromatic polycarboxylic acids or derivatives thereof. The process can be carried out at low pressure and low temperature to give the corresponding alicyclic polycarboxylic acids or derivatives thereof. The process is performed in the presence of a catalyst, the catalyst contains a catalyst support and an active metal, wherein the catalyst support comprises groups IIA and IIIA elements of the periodic table, and the active metal comprises group VIII B transition metal elements of the periodic table, and further comprises oxygen or oxygenated chemicals. Compared with the conventional methods, generally, hydrogenation reaction needs to be carried out in a high-pressure hydrogen environment and at a suitable temperature, so that the catalyst can exhibit its catalytic activity. Although increasing the reaction temperature can increase the reaction rate as well as the conversion, however, it is easy to cause a side reaction and bring about a decrease in the purity of the products. Moreover, because the hydrogenated products, alicyclic polycarboxylic acids or their derivatives, and the original reactants-aromatics polycarboxylic acids or their derivatives, are similar in structure, they cannot be easily separated. The present invention majorly enhances the activity of the catalyst without compromising the purity of the products by using the catalyst. Therefore, it can be understood that the process of the present invention has substantial advantages compared with the prior art. One of the advantages is that using the process, the conversion can higher than 99.9% at a temperature only between 50 and 100° C., and the pressure between 1 and 30 bar. Another advantage is that the product selectivity can be enhanced to over 99%, which can reduce the cost of subsequent separation and improve the overall economic benefit.

The process provided by the present invention is performed in the presence of the catalyst. The catalyst has a catalyst support and an active metal, wherein the catalyst support comprises group IIA elements and group IVA elements of the periodic table. The group IIA elements comprise magnesium (Mg), calcium (Ca), strontium (Sr), barium (Ba) or combinations of thereof, and group IVA elements comprise silicon (Si), germanium (Ge), Tin (Sn) or combinations of thereof. The active metal comprise group VIII B transition metal elements of the periodic table, comprising nickel (Ni), platinum (Pt), palladium (Pd), ruthenium (Ru), rhodium (Rh) or combinations thereof.

Wherein the active metal of group VIIIB transition elements account for 10-80 wt % of the catalyst, the catalyst support of group IIA accounts for 1-30 wt % of the catalyst, the catalyst support of group IVA accounts for 1-30 wt % of the catalyst and the other component of the catalyst is an oxygen or an oxygenated compound. Preferably, the active metal is nickel (Ni), and the active metal accounts for 20-70 wt %, which preferably accounts for 45-65 wt % and further preferably accounts for 50-65 wt %; group IIA accounts for 1-20 wt %, preferably accounts for 2-15 wt % and further preferably accounts for 3-10 wt %; group IVA accounts for 1-20 wt %, preferably accounts for 2-15 wt % and further preferably accounts for 5-12 wt %.

Wherein, in the catalyst, the active metal of group VIIIB transition elements, the catalyst support of group IIA elements and the catalyst support of group IVA elements are in the ratio of (10-80):(1-30):(1-30). When the active metals of group VIIIB transition element is Ni, the catalyst support of group IIA elements is Mg and the catalyst support of group IVA elements is Si, the active metals of group VIIIB transition elements, the catalyst support of group IIA and the catalyst support of group IVA are in the ratio of (20-70):(1-20):(1-20), and preferably are in the ratio of (45-65):(2-15):(2-15), and further preferably are in the ratio of (50-65):(3-10):(5-12). The process provided by the present invention is carried out in the present of the catalyst. The specific surface area of the catalyst is between 80-300 m$^2$/g, and preferably is between 100-250 m$^2$/g, and further preferably is between 120-200 m$^2$/g. The pore volume of the catalyst is between 0.2-0.9 cm$^3$/g, and preferably is between 0.25-0.7 cm$^3$/g, and further preferably is between 0.3-0.5 cm$^3$/g. The average pore size diameter of the catalyst is between 2-50 nm, and preferably is between 5-30 nm, and further preferably is between 10-25 nm.

The reaction process provided by the present invention can be carried out in the presence of solvent or other diluent. In order to avoid phase separation or immiscibility, compatibility of the solvent or diluent with the main reactants shall be taken into consider when selecting the solvent or diluent, and the solvent or diluent should not participate in the reaction under hydrogenation condition. The hydrogenation products themselves can also be used as solvent or diluent. The solvent used in the present invention comprises isopropanol, n-butanol, isobutanol, 2-ethyl hexanol, isononyl alcohol, tetrahydrofuran, n-hexanol etc.

The reactor used in the present process can be a continuous trickle bed reactor, a stir tank reactor, a multi-tube reactor or a non-continuous reactor such as batch reactor.

DETAILED DESCRIPTION OF THE PREFERRED EMBODIMENT

Preparation Example 1: Preparation of Catalyst A 53.5 g of nickel nitrate and 9.5 g of magnesium nitrate were dissolved and mixed in 300 mL of deionized water to form a solution. Next, deionized water containing ammonia water, sodium carbonate or sodium hydroxide (or a mixture of any two of above), were added into the solution for adjusting pH to 9-11 and stirred completely at 60-90° C. 6 mL of sodium silicate solution was subsequently added into the above solution and continuously stirred for 1-4 hours. The stirred solution was then filtered to give a filter cake. After washed and dried at 110° C., the filter cake was calcined at 700° C. for 4 hours to obtain a catalyst A.

Preparation Example 2: Preparation of Catalyst B 53.5 g of nickel nitrate and 19.1 g of magnesium nitrate were dissolved and mixed in 300 mL of deionized water to form a solution. Next, deionized water containing ammonia water, sodium carbonate or sodium hydroxide (or a mixture of any two of above), were added into the solution for adjusting pH to 9-11 and stirred completely at 60-90° C. 24 mL of sodium silicate solution was subsequently added into the above solution and continuously stirred for 1-4 hours. The stirred solution was then filtered to give a filter cake. After washed and dried at 110° C., the filter cake was calcined at 700° C. for 4 hours to obtain a catalyst B.

The present invention provides a hydrogenation reaction of aromatic polycarboxylic acids and derivatives thereof using the catalyst containing a catalyst support and active metals. The hydrogenation reaction is carried out using di(2-ethylhexyl) phthalate (DEHP), dibutyl phthalate (DBP) and diisononyl phthalate (DINP) as reactants. The reaction conditions and results are described as follows.

Embodiment 1

7 mL of the catalyst A (20-30 mesh size) was filled in a reaction tube and reduced at 450° C. in hydrogen atmosphere. After cooling, the reactor was fed with di(2-ethylhexyl) phthalate (DOP, DEHP) by pump to perform hydrogenation reaction. After the reaction, the products were collected for quantitative measurement. The conversion and selectivity were analyzed by liquid chromatography-UV (LC-UV) and gas chromatograph (GC), respectively. The operating conditions and the corresponding results are shown in Table 1:

TABLE 1

| Reactant | Reaction pressure (Bar) | Reaction temperature (° C.) | Flow rate of reactants (ml/min) | Flow rate of hydrogen (L/hr) | Conversion (%) | Selectivity (%) |
|---|---|---|---|---|---|---|
| DOP | 20 | 80 | 0.018 | 1.7 | 99.98 | 99.8 |
|  | 10 | 90 | 0.018 | 1.7 | 99.98 | 99.7 |

Embodiment 2

7 mL of the catalyst B (20-30 mesh size) was filled in a reaction tube and reduced at 450° C. in hydrogen atmosphere. After cooling, the reactor was fed with dibutyl phthalate (DBP) by pump to perform hydrogenation reaction. After the reaction, the products were collected for quantitative measurement. The conversion and selectivity were analyzed by liquid chromatography-UV (LC-UV) and gas chromatograph (GC), respectively. The operating conditions and the corresponding results are shown in Table 2:

TABLE 2

| Reactant | Reaction pressure (Bar) | Reaction temperature (° C.) | Flow rate of reactants (ml/min) | Flow rate of hydrogen (L/hr) | Conversion (%) | Selectivity (%) |
|---|---|---|---|---|---|---|
| DBP | 20 | 70 | 0.018 | 1.7 | 99.96 | 99.7 |
|  | 10 | 80 | 0.018 | 1.7 | 99.97 | 99.7 |

Embodiment 3

7 mL of the catalyst B (20-30 mesh size) was filled in a reaction tube and reduced at 450° C. in hydrogen atmosphere. After cooling, the reactor was fed with dibutyl phthalate (DBP) and 1-Butanol (as a solvent), in ratio 1:1 by weight, by pump to perform hydrogenation reaction. After the reaction, the products were collected for quantitative measurement. The conversion and selectivity were analyzed by liquid chromatography-UV (LC-UV) and gas chromatograph (GC), respectively. The operating conditions and the corresponding results are shown in Table 3:

TABLE 3

| Reactant | Reaction pressure (Bar) | Reaction temperature (° C.) | Flow rate of reactants (ml/min) | Flow rate of hydrogen (L/hr) | Conversion (%) | Selectivity (%) |
|---|---|---|---|---|---|---|
| DBP and 1-butanol mixed solution (mix ratio: 1:1 by weight) solution | 20 | 70 | 0.042 | 3.2 | 99.98 | 99.6 |
|  | 10 | 80 | 0.042 | 3.2 | 99.98 | 99.4 |

Embodiment 4

7 mL of the catalyst B (20-30 mesh size) was filled in a reaction tube and reduced at 450° C. in hydrogen atmosphere. After cooling, the reactor was fed with di(2-ethylhexyl) phthalate (DOP or DEHP) by pump to perform hydrogenation reaction. After the reaction, the products were collected for quantitative measurement. The conversion and selectivity were analyzed by liquid chromatography-UV (LC-UV) and gas chromatograph (GC), respectively. The operating conditions and the corresponding results are shown in Table 4:

TABLE 4

| Reactant | Reaction pressure (Bar) | Reaction temperature (° C.) | Flow rate of reactants (ml/min) | Flow rate of hydrogen (L/hr) | Conversion (%) | Selectivity (%) |
|---|---|---|---|---|---|---|
| DOP | 20 | 70 | 0.016 | 1.5 | 99.99 | 99.8 |
|  | 10 | 80 | 0.016 | 1.5 | 99.99 | 99.7 |

Embodiment 5

7 mL of the catalyst B (20-30 mesh size) was filled in a reaction tube and reduced at 450° C. in hydrogen atmosphere. After cooling, the reactor was fed with di(2-ethylhexyl) phthalate (DOP) and 2-ethyl-hexanol (as a solvent), in ratio 1:1 by weight, by pump to perform hydrogenation reaction. After the reaction, the products were collected for quantitative measurement. The conversion and selectivity were analyzed by liquid chromatography-UV (LC-UV) and gas chromatograph (GC), respectively. The operating conditions and the corresponding results are shown in Table 5:

TABLE 5

| Reactant | Reaction pressure (Bar) | Reaction temperature (° C.) | Flow rate of reactants (ml/min) | Flow rate of hydrogen (L/hr) | Conversion (%) | Selectivity (%) |
|---|---|---|---|---|---|---|
| DOP and 2-ethylhexanol mixed solution (mix ratio: 1:1 by weight) | 20 | 70 | 0.039 | 3.0 | 99.98 | 99.7 |
|  | 10 | 75 | 0.039 | 3.0 | 99.99 | 99.7 |

Embodiment 6

7 mL of the catalyst B (20-30 mesh size) was filled in a reaction tube and reduced at 450° C. in hydrogen atmosphere. After cooling, the reactor was fed with di-isononyl phthalate (DINP) by pump to perform hydrogenation reaction. After the reaction, the products were collected for quantitative measurement. The conversion and selectivity were analyzed by liquid chromatography-UV (LC-UV) and gas chromatograph (GC), respectively. The operating conditions and the corresponding results are shown in Table 6:

TABLE 6

| Reactant | Reaction pressure (Bar) | Reaction temperature (° C.) | Flow rate of reactants (ml/min) | Flow rate of hydrogen (L/hr) | Conversion (%) | Selectivity (%) |
|---|---|---|---|---|---|---|
| DINP | 20 | 70 | 0.019 | 1.7 | 99.98 | 99.7 |
|  | 10 | 80 | 0.019 | 1.7 | 99.99 | 99.7 |

Embodiment 7

7 mL of the catalyst B (20-30 mesh size) was filled in a reaction tube and reduced at 450° C. in hydrogen atmosphere. After cooling, the reactor was fed with di-isononyl phthalate (DINP) and isononyl alcohol (as a solvent), in ratio 1:1 by weight, by pump to perform hydrogenation reaction. After the reaction, the products were collected for quantitative measurement. The conversion and selectivity were analyzed by liquid chromatography-UV (LC-UV) and gas chromatograph (GC). The operating conditions and the corresponding results are shown in Table 7:

TABLE 7

| Reactant | Reaction pressure (Bar) | Reaction temperature (° C.) | Flow rate of reactants (ml/min) | Flow rate of hydrogen (L/hr) | Conversion (%) | Selectivity (%) |
|---|---|---|---|---|---|---|
| DINP and isononyl alcohol mixed solution (mix ratio: 1:1) | 20 | 70 | 0.045 | 4.1 | 99.99 | 99.8 |
|  | 10 | 80 | 0.045 | 4.1 | 99.99 | 99.7 |

What is claimed is:

1. A process for hydrogenation of aromatic polycarboxylic acids or derivatives thereof to the corresponding alicyclic polycarboxylic acids or derivatives thereof by hydrogenation of aromatic polycarboxylic acids or derivatives thereof with a catalyst in hydrogen atmosphere, wherein the catalyst comprises (1) an active metal of group VIIIB transition elements of the periodic table and (2) a catalyst support made from a combination of group IIA and group IVA elements of the periodic table.

2. The process for hydrogenation of aromatic polycarboxylic acids or derivatives thereof to the corresponding alicyclic polycarboxylic acids or derivatives thereof as claimed in claim 1, wherein the active metal of the group VIIIB transition elements of the periodic table is platinum (Pt), palladium (Pd), ruthenium (Ru), nickel (Ni), rhodium (Rh) or any combination of the above.

3. The process for hydrogenation of aromatic polycarboxylic acids or derivatives thereof to the corresponding alicyclic polycarboxylic acids or derivatives thereof as claimed in claim 1, wherein the catalyst support of group IIA elements of the periodic table is magnesium (Mg), calcium (Ca), strontium (Sr), barium (Ba) or any combination of the above.

4. The process for hydrogenation of aromatic polycarboxylic acids or derivatives thereof to the corresponding alicyclic polycarboxylic acids or derivatives thereof as claimed in claim 1, wherein the catalyst support of group IVA elements of the periodic table is silicon (Si), germanium (Ge), Tin (Sn) or any combination of the above.

5. The process for hydrogenation of aromatic polycarboxylic acids or derivatives thereof to the corresponding alicyclic polycarboxylic acids or derivatives thereof as claimed in claim 1, wherein the active metal of group VIIIB transition elements, the catalyst support of group IIA elements and the catalyst support of group IVA elements are in the ratio of (10-80):(1-30):(1-30).

6. The process for hydrogenation of aromatic polycarboxylic acids or derivatives thereof to the corresponding alicyclic polycarboxylic acids or derivatives thereof as claimed in claim 1, wherein when the active metal of group VIIIB transition element is Ni, the catalyst support of group IIA elements is Mg and the catalyst support of group IVA elements is Si, the active metal of group VIIIB transition elements, the catalyst support of group IIA and the catalyst support of group IVA are in the ratio of (20-70):(1-20):(1-20).

7. The process for hydrogenation of aromatic polycarboxylic acids or derivatives thereof to the corresponding alicyclic polycarboxylic acids or derivatives thereof as claimed in claim 1, wherein when the active metals of group VIIIB transition elements is Ni, the catalyst support of group IIA elements is Mg and the catalyst support of group IVA elements is Si, the active metal of group VIIIB transition elements, the catalyst support of group IIA and the catalyst support of group IVA are in the ratio of (45-65):(2-15):(2-15).

8. The process for hydrogenation of aromatic polycarboxylic acids or derivatives thereof to the corresponding alicyclic polycarboxylic acids or derivatives thereof as claimed in claim 1, wherein when the active metals of group VIIIB transition element is Ni, the catalyst support of group IIA elements is Mg and the catalyst support of group IVA elements is Si, the active metal of group VIIIB transition elements, the catalyst support of group IIA and the catalyst support of group IVA are in the ratio of (50-65):(3-10):(5-12).

9. The process for hydrogenation of aromatic polycarboxylic acids or derivatives thereof to the corresponding alicyclic polycarboxylic acids or derivatives thereof as claimed in claim 1, wherein the to specific surface area of the catalyst is between 80-300 $m^2/g$, the pore volume of the catalyst is between 0.2-0.9 $cm^3/g$, and the average pore size diameter of the catalyst is between 2-50 nm.

10. The process for hydrogenation of aromatic polycarboxylic acids or derivatives thereof to the corresponding alicyclic polycarboxylic acids or derivatives thereof as claimed in claim 1, wherein the specific surface area of the catalyst is between 100-250 $m^2/g$, the pore volume of the catalyst is between 0.25-0.7 $cm^3/g$, and the average pore size diameter of the catalyst is between 5-30 nm.

11. The process for hydrogenation of aromatic polycarboxylic acids or derivatives thereof to the corresponding alicyclic polycarboxylic acids or derivatives thereof as claimed in claim 1, wherein the specific surface area of the catalyst is between 120-200 $m^2/g$, the pore volume of the catalyst is between 0.3-0.5 $cm^3/g$, and the average pore size diameter of the catalyst is between 10-25 nm.

12. The process for hydrogenation of aromatic polycarboxylic acids or derivatives thereof to the corresponding alicyclic polycarboxylic acids or derivatives thereof as claimed in claim 1, wherein the aromatic polycarboxylic acids are aromatic compounds form with carboxylic acids, dicarboxylic acids, polycarboxylic acids, hydroxycarboxylic acids or any combination of above in structure, and benzene polycarboxylic acids comprise phthalic acids, isophthalic acids, terephthalic acids, trimellitic acids, trimesic acids, hemimellitic acids, pyromellitic acids, or any combination of the above.

13. The process for hydrogenation of aromatic polycarboxylic acids or derivatives thereof to the corresponding alicyclic polycarboxylic acids or derivatives thereof as claimed in claim 1, wherein the derivatives of aromatic polycarboxylic acids comprise monoesters, diesters and polyesters of aromatic polycarboxylic acids or any combination of the above, wherein the esters comprise $C_1$-$C_{30}$ alkyl esters, $C_3$-$C_{30}$ cycloalkyl esters, $C_1$-$C_{30}$ alkoxyalkyl esters or any combination of the above.

14. The process for hydrogenation of aromatic polycarboxylic acids or derivatives thereof to the corresponding alicyclic polycarboxylic acids or derivatives thereof as claimed in claim 1, wherein the derivatives of aromatic polycarboxylic acids are esters comprising $C_2$-$C_{20}$ alkyl esters, $C_3$-$C_{20}$ cycloalkyl esters, $C_2$-$C_{20}$ alkoxyalkyl esters or any combination of the above.

15. The process for hydrogenation of aromatic polycarboxylic acids or derivatives thereof to the corresponding alicyclic polycarboxylic acids or derivatives thereof as claimed in claim 1, wherein the derivatives of aromatic polycarboxylic acids are esters comprising $C_3$-$C_{18}$ alkyl esters, $C_4$-$C_{18}$ cycloalkyl esters, $C_3$-$C_{18}$ alkoxyalkyl esters or any combination of the above.

16. The process for hydrogenation of aromatic polycarboxylic acids or derivatives thereof to the corresponding alicyclic polycarboxylic acids or derivatives thereof as claimed in claim 1, wherein the derivatives of aromatic polycarboxylic acids comprise dimethyl phthalate (DMP), dimethyl terephthalate (DMT), dimethyl isophthalate, diethyl phthalate (DEP), dibutyl phthalate (DBP), diisooctyl phthalate (DOP), diisononyl phthalate (DINP), benzyl butyl phthalate (BBP), diisodecyl phthalate (DIDP), dioctyl terephthalate (DOTP) or any combination of the above.

17. The process for hydrogenation of aromatic polycarboxylic acids or derivatives thereof to the corresponding alicyclic polycarboxylic acids or derivatives thereof as claimed in claim 1, wherein the hydrogenation is carried out at pressure between 1-100 bar.

18. The process for hydrogenation of aromatic polycarboxylic acids or derivatives thereof to the corresponding alicyclic polycarboxylic acids or derivatives thereof as claimed in claim 1, wherein the hydrogenation is carried out at pressure between 1-50 bar.

19. The process for hydrogenation of aromatic polycarboxylic acids or derivatives thereof to the corresponding alicyclic polycarboxylic acids or derivatives thereof as claimed in claim 1, wherein the hydrogenation is carried out at pressure between 1-30 bar.

20. The process for hydrogenation of aromatic polycarboxylic acids or derivatives thereof to the corresponding alicyclic polycarboxylic acids or derivatives thereof as claimed in claim 1, wherein the hydrogenation is carried out at temperature between 50-200° C.

21. The process for hydrogenation of aromatic polycarboxylic acids or derivatives thereof to the corresponding alicyclic polycarboxylic acids or derivatives thereof as claimed in claim 1, wherein the hydrogenation is carried out at temperature between 50-150° C.

22. The process for hydrogenation of aromatic polycarboxylic acids or derivatives thereof to the corresponding alicyclic polycarboxylic acids or derivatives thereof as claimed in claim 1, wherein the hydrogenation is carried out at temperature between 50-100° C.

23. The process for hydrogenation of aromatic polycarboxylic acids or derivatives thereof to the corresponding alicyclic polycarboxylic acids or derivatives thereof as claimed in claim 1, wherein the aromatic polycarboxylic acids or derivatives thereof can be mixed with solvent or diluent.

24. The process for hydrogenation of aromatic polycarboxylic acids or derivatives thereof to the corresponding alicyclic polycarboxylic acids or derivatives thereof as claimed in claim 1, wherein operating type of the process comprises batch type, semi-batch type, continuous type or any combination of the above.

25. The process for hydrogenation of aromatic polycarboxylic acids or derivatives thereof to the corresponding alicyclic polycarboxylic acids or derivatives thereof as claimed in claim 1, wherein the hydrogenation is carried out in a reactor comprising a batchwise, stir tank, trickle bed, bubble column, multi-tube or any combination of the above.

* * * * *